(12) United States Patent
Zhou et al.

(10) Patent No.: US 7,727,776 B2
(45) Date of Patent: Jun. 1, 2010

(54) CORE-SHELL NANOPARTICLES FOR DETECTION BASED ON SERS

(75) Inventors: Jicang Zhou, Shanghai (CN); Yuandong Gu, Plymouth, MN (US); Allen A. Cox, Minneapolis, MN (US); Aravind Padmanabhan, Plymouth, MN (US)

(73) Assignee: Honeywell International Inc., Morristown, NJ (US)

(*) Notice: Subject to any disclaimer, the term of this patent is extended or adjusted under 35 U.S.C. 154(b) by 689 days.

(21) Appl. No.: 11/552,383

(22) Filed: Oct. 24, 2006

(65) Prior Publication Data
US 2008/0096289 A1 Apr. 24, 2008

(51) Int. Cl.
*G01N 33/551* (2006.01)

(52) U.S. Cl. .................. 436/524; 435/6; 436/164; 436/525

(58) Field of Classification Search .................. None
See application file for complete search history.

(56) References Cited

U.S. PATENT DOCUMENTS

| | | | |
|---|---|---|---|
| 4,313,734 A * | 2/1982 | Leuvering | 436/525 |
| 5,255,067 A | 10/1993 | Carrabba et al. | |
| 5,266,498 A | 11/1993 | Tarcha et al. | |
| 6,040,191 A | 3/2000 | Grow | |
| 6,043,034 A | 3/2000 | Takama et al. | |
| 6,149,868 A | 11/2000 | Natan et al. | |
| 6,174,677 B1 | 1/2001 | Vo-Dinh | |
| 6,219,137 B1 | 4/2001 | Vo-Dinh | |
| 6,406,777 B1 | 6/2002 | Boss et al. | |
| 6,514,767 B1 | 2/2003 | Natan | |
| 6,623,977 B1 | 9/2003 | Farquharson et al. | |
| 6,649,683 B2 | 11/2003 | Bell | |
| 6,699,724 B1 | 3/2004 | West et al. | |
| 6,858,372 B2 | 2/2005 | Whitlock et al. | |
| 6,878,184 B1 | 4/2005 | Rockenberger et al. | |
| 6,947,132 B1 | 9/2005 | Boss et al. | |
| 7,019,828 B2 | 3/2006 | Su et al. | |
| 2003/0187237 A1 | 10/2003 | Chan et al. | |
| 2004/0023411 A1 | 2/2004 | Fenn | |
| 2004/0038255 A1 | 2/2004 | Mirkin et al. | |
| 2004/0086897 A1* | 5/2004 | Mirkin et al. | 435/6 |
| 2004/0110208 A1 | 6/2004 | Chan et al. | |
| 2004/0174520 A1 | 9/2004 | Premasiri et al. | |
| 2004/0191669 A1 | 9/2004 | Whitlock et al. | |
| 2005/0147963 A1 | 7/2005 | Su et al. | |
| 2005/0191665 A1 | 9/2005 | Su et al. | |

(Continued)

OTHER PUBLICATIONS

Bizzarri et al., "Surface-Enhanced Resonance Raman Spectroscopy Signals from Single Myoglobin Molecules," Applied Spectroscopy, vol. 56, No. 12, pp. 1531-1537, 2002.

(Continued)

*Primary Examiner*—Christopher L Chin
(74) *Attorney, Agent, or Firm*—Crompton Seager & Tufte, LLC (57) ABSTRACT

A nanoparticle having a self assembly monolayer of molecules as a shell on the nanoparticle. The monolayer may include organic molecules working as surface enhanced Raman spectroscopy (SERS) reporters. Also, the core shell may include at least a receptor, and/or the like, to ensure that a target analyte can be bound for measurement with SERS. The target analyte may be organic, chemical, biological, inorganic, gas, liquid, solid, and so forth.

15 Claims, 7 Drawing Sheets

U.S. PATENT DOCUMENTS

2005/0196870 A1    9/2005    Sun
2005/0201941 A1    9/2005    Cho et al.
2005/0226938 A1    10/2005    Borbely et al.

OTHER PUBLICATIONS

Cooks et al., "Ambient Mass Spectrometry," Science, vol. 311, pp. 1566-1570, Mar. 17, 2006.

Elechiguerra et al., Interaction of silver nanoparticles with HIV-1, Journal of Nanobiotechnology, pp. 1-10, Mar. 28, 2005.

Etchegoin et al., New limits in ultrasensitive trace detection by surface enhanced Raman scattering (SERS), Elsevier Science B.V., pp. 84-90, Jan. 6, 2003.

Kelly et al., "The Optical Properties of Metal Nanoparticles: The Influence of Size, Shape, and Dielectric Environment," J. Phys. Chem B, vol. 107, No. 3, pp. 668-677, Aug. 9, 2003.

Kneipp et al., "Surface-Enhanced Raman Spectroscopy in Single Living Cells Using Gold Nanoparticles," Applied Spectroscopy, vol. 56, No. 2, pp. 150-154, 2002.

Li et al., "Electroreduction Activity of Hydrogen Peroxide on Pt and Au Electrodes," American Chemical Society, vol. 21, No. 20, pp. 9251-9259, 2005.

Ooka et al., "Surface-Enchanced Raman Spectroscopy of DOPA-Containing Peptides Related to Adhesive Protein of Marine Mussel, Mytilus Edulis," Biopolymers, vol. 57, pp. 92-102, 2000.

Sengupta et al., "Surface-Enhanced Raman Spectroscopy of Bacteria and Pollen," Applied Spectroscopy, vol. 59, No. 8, 2005.

Real-Time Analyzers, "Simple SERS Sample Vials," 2 pages, Mar. 3, 2003.

Wilke et al.,"Surface-Enhanced Raman Spectroscopy as a Probe of Adsorption at Transition Metal-High-Pressure Gas Interfaces: NO, CO, and Oxygen on Platinum-, Rhodium-, and Ruthenium-Coated Gold," American Chemical Society, vol. 7, No. 4, pp. 714-721, 1991.

Zeng et al., "Electro-Hydrodynamic Modeling of Electrospray Ionization: CAD for a Fluidic Device—Mass Spectrometer Interface," 5 pages, prior to Sep. 21, 2006.

\* cited by examiner

CORE-SHELL NANOPARTICLES FOR DETECTION BASED ON SERS

BACKGROUND

The invention pertains to detection systems, and particularly to detection systems incorporating Raman spectroscopy scattering. More particularly, the invention pertains to detection systems using surface enhanced Raman spectroscopy.

SUMMARY

The present invention is a detection system having core-shell nanoparticles for ultrasensitive detection based on enhanced Raman spectroscopy.

DESCRIPTION

In various areas, such as biomedical diagnostics, environmental monitoring (e.g., water quality), including analyses of food, biological, gas, chemical, organic and inorganic analytes, and so forth; there may be a need for ultra-sensitive detection techniques. Such techniques may be effected with Raman spectroscopy and particularly with surface enhanced Raman scattering or spectroscopy (SERS) with core-shell nanoparticles for enhancement. Raman spectroscopy along with SERS may provide a unique spectrum or intrinsic signature (i.e., "fingerprint") of the matter or analytes being detected, examined and/or analyzed. SERS permits one to directly detect and examine analytes without the need of markers or tags (e.g., indirect techniques involving fluorescence). The present core-shell nanoparticle approach based on SERS is a cheaper, simpler, very elegant and ultra-sensitive detection technology, relative to related-art technologies.

To lead into the present system, it may be noted that when light is scattered from an atom or molecule, most photons are elastically scattered (i.e., Rayleigh scattering). The scattered photons may have the same frequency as the incident photons. However, a small fraction of light (e.g., about 1 in $10^{12}$ photons) may be scattered at frequencies different from the frequency of the incident photons. This may be a result of inelastic scattering. Such scattered light may provide information about the molecules' vibrational quantum states. Raman scattering may involve light scattering at different wavelengths to the incident light. Because individual substances have a unique Raman spectrum, such scattering may be an excellent identification tool.

However, Raman signals may be characteristically weak since as noted herein that approximately 1 in $10^{12}$ incident photons may be scattered with a shift in wavelength. The signals may be enhanced by two processes. In one process, resonance Raman scattering, the laser may be tuned to the absorbance of the substance of interest. The other process, surface-enhanced Raman scattering, requires the substance to be in close proximity to a metal surface, exploiting the surface plasmon resonance (SPR) properties of suitable materials (e.g., gold, silver or copper nanoparticles). Surface enhancement may produce signal amplification of $10^5$-$10^6$. Combining these two processes, called surface-enhanced resonance Raman scattering (SERRS), can be a sensitive technique that may produce signal amplification of up to $10^{14}$ and be capable of single molecule detection. This SERRS technique may also be referred to herein as SERS.

Figure 1:
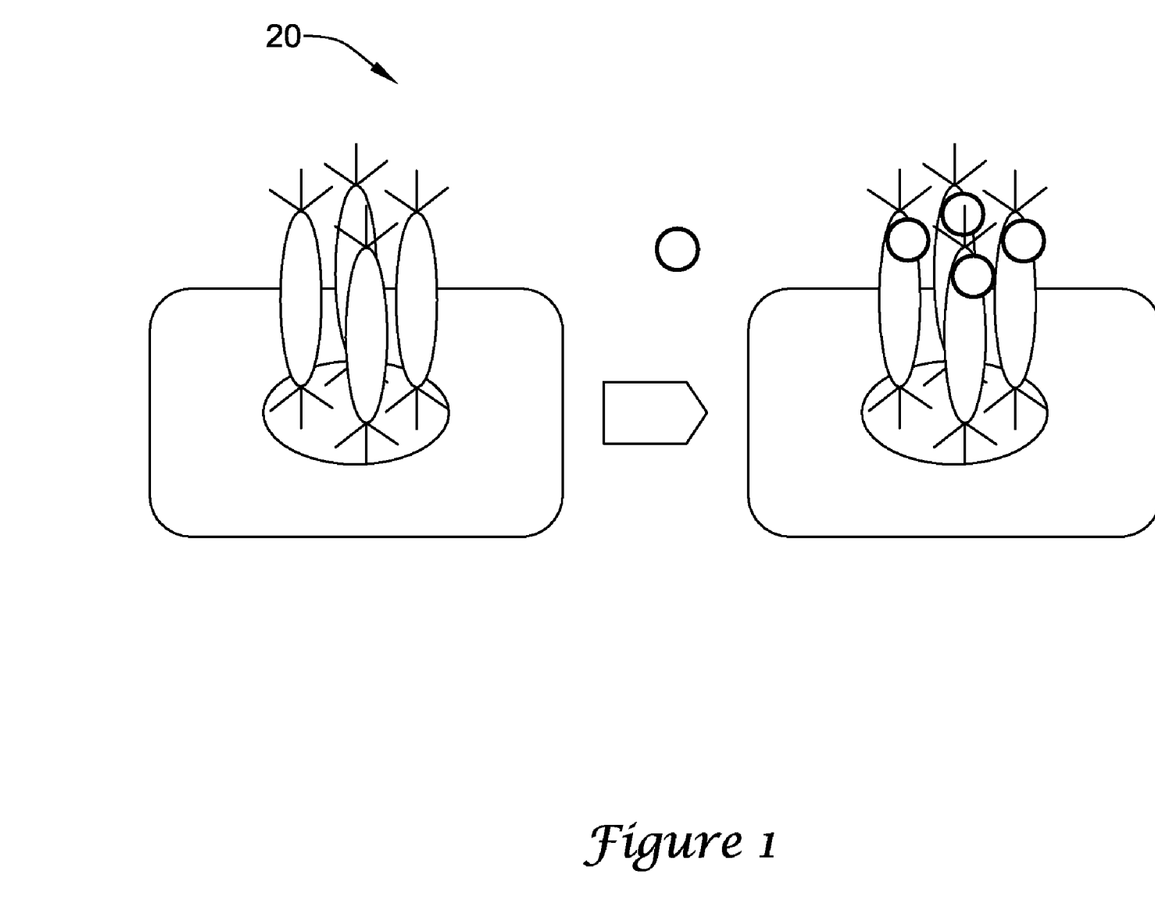
FIG. 1 is a diagram of SERS based ultrasensitive detection using core-shell nanoparticle optical probes.

SERS based ultrasensitive detection and the SERS active substrates may be regarded as an important enabling technology. FIG. 1 is a schematic presentation of an ultrasensitive detection system 20 based on SERS, which may involve the following steps. First, samples from various sources may be subjected to suitable preparation procedures like purification, concentration, and so forth. The product thereof containing extremely low concentration of target molecules may then be captured to a substrate via selective binding. Hereafter, the captured target molecules may be labeled via SERS optical probes and be followed by Raman measurement.

Figure 2:
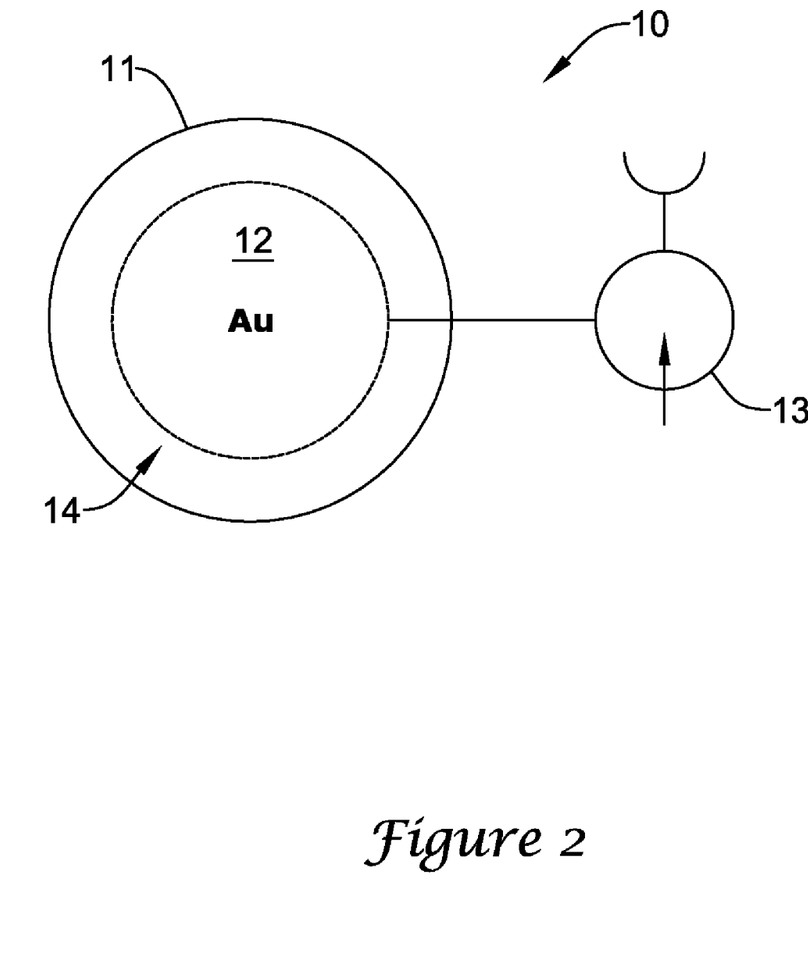
FIG. 2 is a diagram of a core-shell nanoparticle surface enhanced Raman scattering or spectroscopy (SERS) probe.

The technology may involve a new type of core-shell nanoparticles as optical probes for ultrasensitive detection based on SERS. The present optical probe 10 may have a core-shell structure 11 with a metal core 12 for SERS active detection (FIG. 2). The shell 11 may have organic molecules working as SERS reporters 14. Additionally, the core-shell nanoparticle 10 may be operational with a receptor 13, DNA probes, and tibodies, oligoglucosides, amino acid sequences, and so on, to ensure that the nanoparticle 10 can selectively bind to a target analyte to be measured. The target analyte may be organic, chemical, biological, inorganic, gas, liquid, solid, and so forth.

This type of nanoparticle structure 10 may have several advantages. For instance, by adjusting the organic molecule structure 14 including a SERS reporter, one may increase the chemical enhancement which is highly desired for ultrasensitive detection.

Another advantage is that by self-assembly of a monolayer (SAM) 14 of organic molecules (i.e., SERS reporters) onto a metal nanoparticle, there may result a making of thousands of Raman scatters on a single nanoparticle. This approach may increase the enhancement factor by several thousand times.

Still another advantage is that the core-shell nanoparticle 10 may be easily modified by other molecules like DNA probes, antibodies, oligoglucosides, amino acid sequences (e.g., RGD receptors), and so forth. That may make it a good optical probe platform for ultrasensitive detection based on SERS for various applications.

A particular application may be effected with chemical, organic, biological, inorganic and/or gas molecules.

Also, the core-shell nanoparticles may address the issue of non-specific binding, which plague many biomedical diagnostics, via creating the biomolecules—resistant functionalities (e.g., polyethylene glycol (PEG) chain) to the SERS reporter. This may be another advantage of such core-shell nanoparticle SERS optical probes.

The nanoparticle SERS probe may have a gold or silver nanoparticle 12, a SAM 14 of SERS reporters and a biomolecule probe such as DNA probes, antibodies, oligoglucosides, or amino acid sequences, and so forth.

It might be noted that nanoparticle SERS probes may be produced for reacting with desired organic, chemical, biological, inorganic, gas, and/or like molecules.

Figure 3:
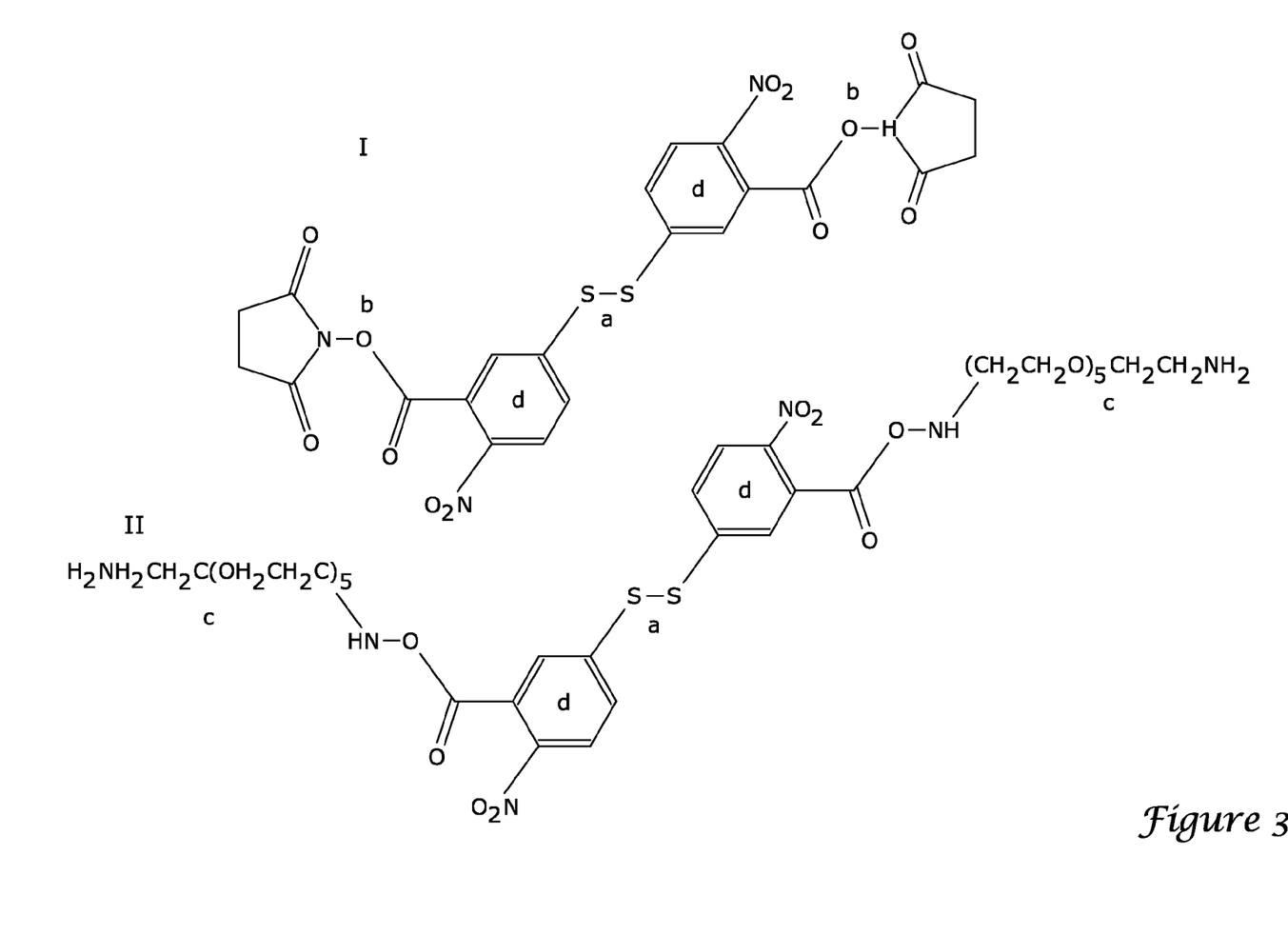
FIG. 3 shows an example of design and synthesis of an organic SERS reporter.

Fabrication of the present nanoparticles may include several steps. A first step may involve a synthesis of functional organics as SERS reporters. At least two types of SERS reporters should be designed and synthesized, both possessing different functional moieties. FIG. 3 shows an example of SERS reporters with different functionalities. Among the functionalities, the first type (a) may be a binding group to ensure its immobilization onto the nanoparticles of silver or gold. In one illustrative example, this can be the sulfur-containing group, e.g., thiol group. The group may be a class of compounds that are analogous to alcohols and phenols but contain sulfur in place of oxygen with the general formula RSH. Alternatively, they can also be thiol ethers or dithiol ethers with the formula of RSSR' or RSR', respectively. In another illustrative example, they can be an amino group (—$NH_2$). One skilled in the art may list more of such groups.

The second type of functionality (b) may be a biomolecule (e.g., DNA or protein) resistant group. In one illustrative example, this can be a PEG (polyethylene glycol) chain. In another illustrative example, this can be a fluorocarbon chain. And in still another illustrative example, this can be a fluorinated PEG chain.

A third type of functionality (c) may be a reactive group to immobilize biomolecular receptors like DNA probes, antibodies, oligoglucosides, and an amino acid sequence, and so forth. Various groups are available to react with biomolecules receptors, e.g., —$NH_2$, —COOH, —CHO, —NCO, and epoxide group, etc. One skilled in the art may be able to list more of such functionalities.

The last type of functionality (d) is a Raman label (Raman reporter). This is the moiety to produce the Raman signals to be detected. The selection of this moiety may therefore be the most important to ensure the desirable performance of the SERS optical probe. Small organic compounds such as thiophenol, mercaptobenzoic acid, and bispyridine were previously used as Raman spectroscopic reporters. These molecules give rise to simple Raman spectra, but it has been difficult or impossible to achieve resonance Raman enhancement at visible excitation wavelengths. As a result, the reported SERS intensities are relatively low, even at high (millimolar) reporter concentrations. On the contrary, various organic dyes, for examples, malachite green isothiocyanate (MGITC), tetramethylrhodamine-5-isothiocyanate (TRITC), X-rhodamine-5-(and -6)-isothiocyanate (XRITC), and 3,3-diethylthiadicarbocyanine iodide (DTDC), have been found to produce very strong Raman signals. Therefore, incorporating such structures into the SERS reporter molecules is one possible approach to make desired SERS reporters. One skilled in the art may understand how to design the synthetic route to make such high performance SERS reporters.

Another consideration may be nanoparticles functionalized for reacting with desired organic, chemical, biological, inorganic, gas, and/or like molecules to result in a nanoparticle SERS probes.

Another illustrative approach to create high performance SERS reporters may be associated with the Raman spectra modeling of organics on a metal surface using software tools like Gaussian 03. This may be a more efficient approach of SERS reporter design.

Consequently, at least two types of SERS reporter molecules may be designed and synthesized. The first one may contain functionalities (a), (b) and (d), and the second one may contain functionalities (a), (c) and (d). One skilled in the art may understand how to proceed with a design and synthesis of the two types of Raman reporter molecules.

Figure 4:
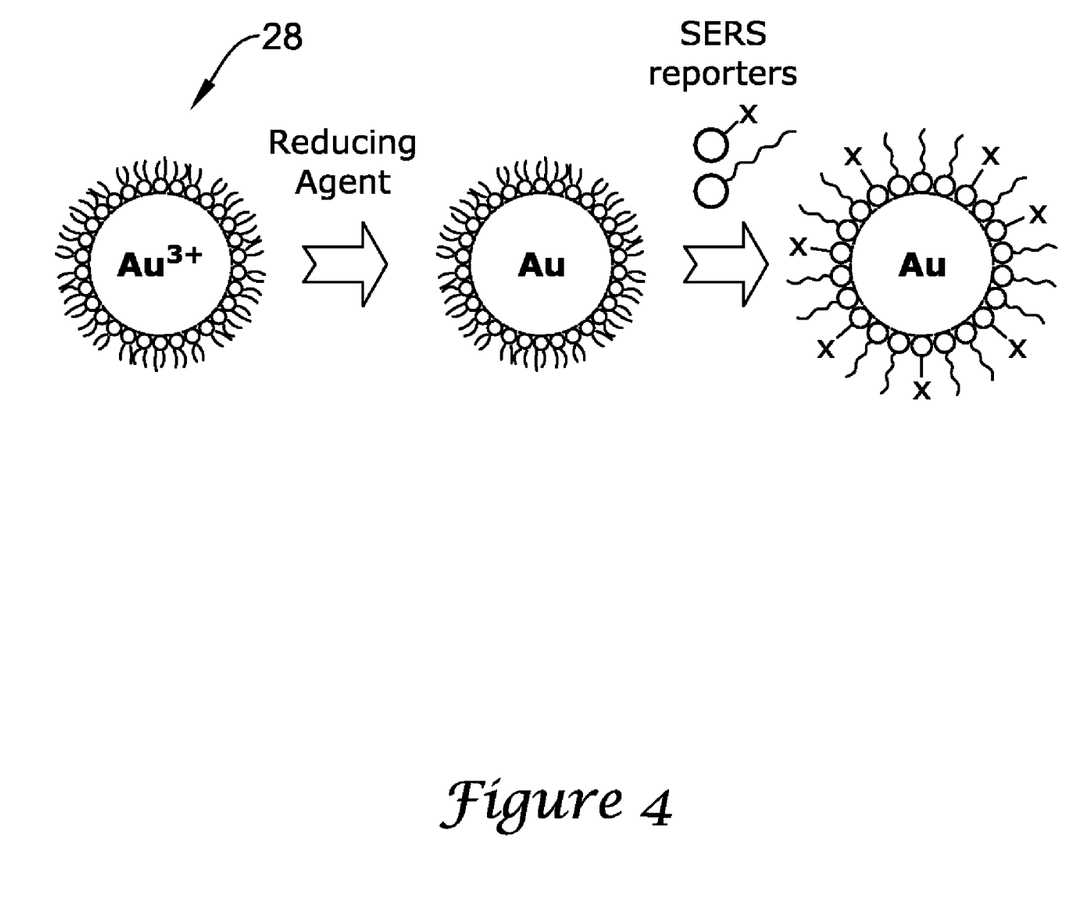
FIG. 4 reveals a synthesis of a nanoparticle and a self assembly of SERS reporters onto a nanoparticle.

The second step of the fabrication of the present nanoparticle SERS probe may involve metal nanoparticle synthesis and functionalization. First, nanoparticles of different metal types (silver or gold), different size and shapes may be synthesized and used to fabricate the SERS optical probe. In one illustrative example, it is a silver nanosphere. In another illustrative example, it is a silver triangle nanoparticle. In another illustrative example, it is a silver nanorod. In still another illustrative example, it is a silver nanoparticle with intrinsic three dimensional (3D) nanopore structures. One skilled in the art may understand that a variety of approaches are available to fabricate the first three types of nanoparticles as these may have been well investigated and reported in certain literature. Here, one novel structure that could be of particular interest to fabricate is the nanoparticle with intrinsic 3D nanopore structures, which may be synthesized via the following procedure. A mixture of Ag/Au precursors ($HAuCl_4$ and $AgNO_3$) is dissolved in deionized water. This is mixed with a surfactant solution, e.g., AOT in hexane, to form an inverse microemulsion. Hereafter, a solution of reducing agents, e.g., $NaBH_4$ in water is added to the microemulsions under vigorous stirring to reduce the metal precursors to nanoparticles of Ag/Au alloy. The nanoparticles are then separated and etched with concentrated nitric acid to create the desired Au nanoparticles with intrinsic 3D nanopore structures. One skilled in the art may understand that other approaches might also be available to make such nanostructures.

The organic SERS reporter molecules noted herein may be immobilized on to the nanoparticles via self-assembly. With this approach, a self-assembly monolayer of organic SERS reporter molecules may be formed around the nanoparticle surface and the nanopore surface in case of nanoparticles with 3D nanopore structures being used as SERS active substrates. This may help to obtain the strongest scattering because more scatters exist onto a single nanoparticle. This self-assembly approach may have been very well investigated and documented in certain literature and one skilled in the art might understand how to use it to make the functionalized nanoparticles comprising SERS reporters and metal nanoparticles.

Figure 5:
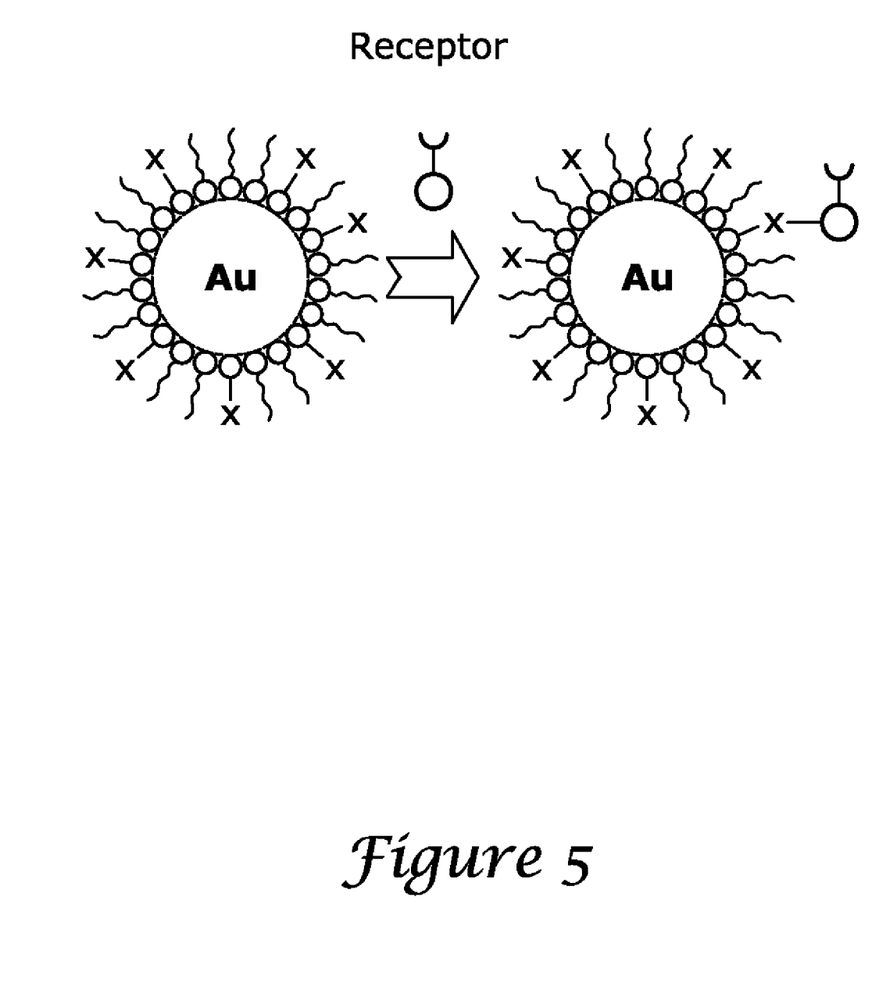
FIG. 5 is a schematic diagram of immobilizing biomolecule probes onto the functionalized metal nanoparticles.

A third step may be where the noted herein functionalized nanoparticles react with the desired biomolecular receptors. FIG. 5 is a schematic diagram showing how to immobilize a biomolecule probe onto the functionalized nanoparticles. Depending on the target applications, different biomolecular receptors can be immobilized. In one illustrative example, the SERS probes in this invention may be used to label DNA targets, and DNA probes need to be immobilized onto the functionalized nanoparticles. In another illustrative example, the SERS probes in this invention may be used to label antigens (e.g., prostate cancer antigen, PSA), and antibodies need to be immobilized. Still in another illustrative example, the SERS probes in this invention may be used to label pathogens, and either oligoglucosides or an amino acid sequence (e.g., RGD) may be immobilized. The chemistry associated with such immobilization appears to have been extensively investigated and one skilled in the art may understand how to design suitable procedures to realize this purpose.

A general approach may be associated with the development of a type of core-shell nanoparticles having a potential application as SERS probes for ultra sensitive detection. A nanoparticle may consist of a metallic core (to ensure the existence of a strong electromagnetic enhancement) and a self-assembly monolayer (SAM) of organic SERS reporters (to provide thousands of Raman scatters on a single nanoparticle). (FIGS. 2 and 3)

The nanoparticles may be further functionalized with various receptors like DNA probes, antibodies, oligoglucosides, or a sequence of amino acid, and so forth, for ultra sensitive detection applications such as biomedical diagnostics, environmental monitoring, plus more. Various targets may be measured; these include DNA targets, protein biomarkers, pathogens, and so on.

For instance, a set of immobilized antibodies may selectively capture target antigens, which are then detected after the directed uptake of gold or silver nanoparticles labeled with both tracer antibodies and intrinsically strong Raman scatters (i.e., Raman reporter molecules).

In another instance, a nanoparticle substrate may be functionalized with antibodies of a specific substance and SERS reporters. A specific substance in a sample may bind with the antibodies. The SERS reporters may be activated and the scattered light may be used to measure the specific substance in the sample.

Figure 6:
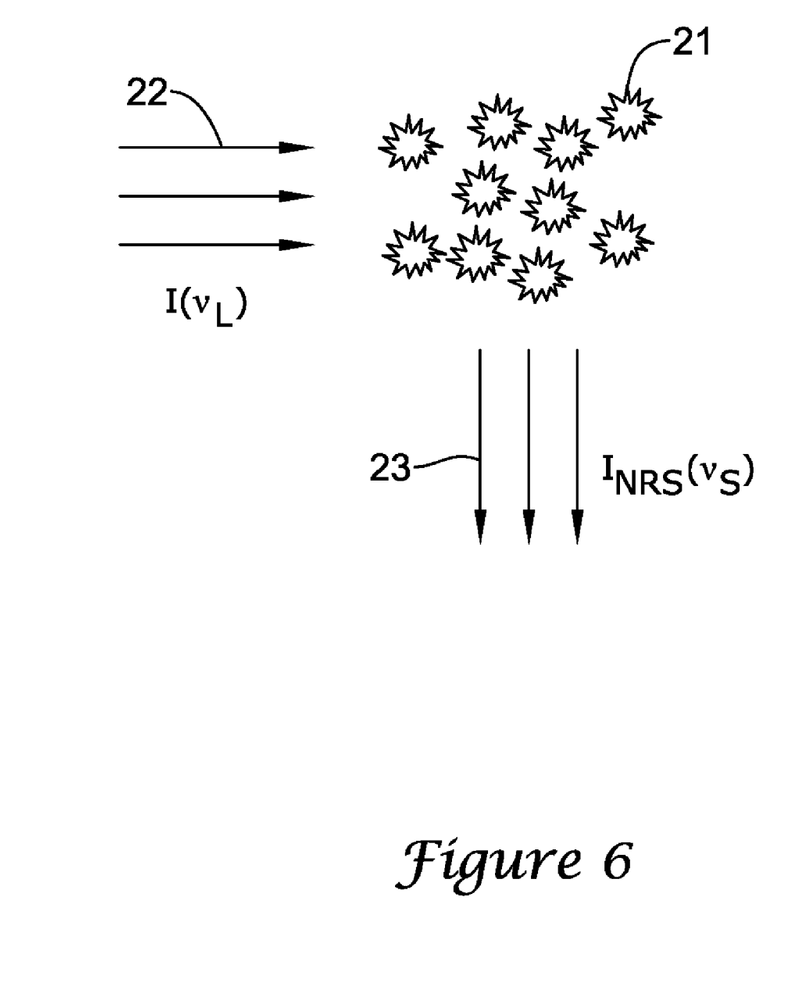
FIGS. 6 and 7 show layouts of normal Raman scattering (NRS) and SERS, respectively.
Figure 7:
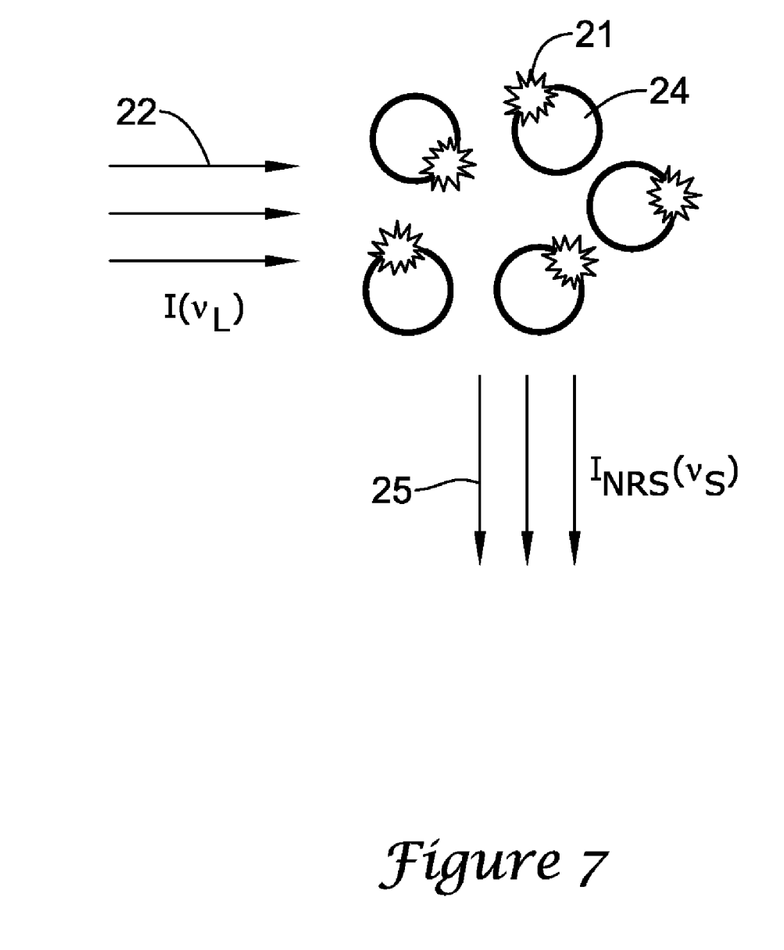

The rationale behind the design of such core-shell nanoparticle optical probes is as follows. FIG. 6 is a schematic representing normal Raman scattering (NRS). FIG. 7 is a schematic representing surface enhanced Raman scattering (SERS). In FIG. 6, molecules 21 may be impinged by light $I(V_L)$ 22 of a magnitude I at a particular frequency $V_L$. There may be a Rayleigh scattering of the light $I_R(V_L)$ (not shown) at a magnitude $I_R$ ($I_{Rayleigh}$) of the same frequency $V_L$. Also, there may be scattered light $I_{NRS}$ ($V_S$) 23 at a magnitude $I_{NRS}$ ($I_{normal\ Raman\ scattering}$) of another frequency $v_S$ other than the frequency $V_L$ of the impinging light $I(V_L)$ 22. The scattered light 23 may be referred to as Raman scattered light. The magnitude $I_{NRS}$ of light 23 is much less (about $10^{12}$) than the magnitude $I_R$ of the Rayleigh scattered light $I_R$ ($V_L$).

In FIG. 7, the molecules 21 may be attached to metal nanoparticles 24. The light $I_R$ ($V_L$) 22 may impinge and be scattered by the molecules 21 on the nanoparticles 24 as light $I_{SERS}$ ($v_S$) 25 having a magnitude $I_{SERS}$ ($I_{surface\ enhanced\ Raman\ scattering}$) at a frequency or frequencies $v_S$ other than the frequency $V_L$ of the incident light 22. The magnitude $I_{SERS}$ of light 25 is much greater than the magnitude $I_{NRS}$ of light 23. The magnitude relationship may be indicated by the following expression, $$I_{NRS}(v_S) << I_{SERS}(v_S).$$

A simple classical electromagnetic field description of Raman spectroscopy may be used to explain many of the important features of Raman band intensities. The dipole moment, μ, induced in a molecule by an external electric field, E, is proportional to the field as shown in the following, $$\mu = \alpha \times E,$$

where, α is the polarizability of the molecule (here it may be termed as the Raman reporters). The polarizability measures the ease with which the electron cloud around a molecule can be distorted. The induced dipole emits or scatters light at the optical frequency of the incident light wave.

Raman scattering occurs because a molecular vibration can change the polarizability. The change is described by the polarizability derivative, $$\frac{\partial \alpha}{\partial Q},$$

where Q is the normal coordinate of the vibration. The selection rule for a Raman-active vibration, that there be a change in polarizability during the vibration, is given in the following equation, $$\frac{\partial \alpha}{\partial Q} \neq 0.$$

The Raman selection rule is analogous to the more familiar selection rule for an infrared-active vibration, which states that there must be a net change in the permanent dipole moment during the vibration. From group theory, it is straightforward to show that if a molecule has a center of symmetry, vibrations which are Raman-active will be silent in the infrared, and vice versa.

Scattering intensity is proportional to the square of the induced dipole moment, and can be expressed using the following equation, $$I^R \propto n|\mu|^2 \approx n(\alpha E)^2,$$

where $I^R$ is the Raman scattering intensity, n is the number of Raman reporters involved in the scattering process, μ is the induced dipoles of the Raman reporter molecules, α is the polarizability of the Raman reporter and E is the strength of the electric field around the Raman reporters.

If a vibration does not greatly change the polarizability, then the polarizability derivative may be near zero, and the intensity of the Raman band will be low. The vibrations of a highly polar moiety, such as the O—H bond, are usually weak. An external electric field can not induce a large change in the dipole moment and stretching or bending the bond does not change this.

The following items are possible solutions to obtain the higher Raman scattering intensity from a nanoparticle SERS probe. First, one may use Raman reporter molecules with higher polarizability (α). Secondly, one may increase the electric field intensity (E) around the Raman reporter molecules via selecting appropriate SERS active substrates. And finally an increase of the number of Raman reporters (n) immobilized on the nanoparticles SERS active substrates may also increase the scattering intensity.

There may be several kinds of enhancement due to the surface enhanced Raman scattering. Electromagnetic enhancement may arise from enhanced local optical fields at the place of the molecule nearby the metal surface due to electromagnetic resonance that appears because of a collective excitation of conduction electrons in the small metallic structures (viz., SPR—surface plasmon resonance). Maximum values from this enhancement may be on the order of $10^6$ to $10^7$ for isolated particles of metals.

The other kind is chemical enhancement. This may include the enhancement of a Raman signal that is related to specific interactions (i.e., electron coupling) between molecules and the metal (substrate), resulting in an "electronic" enhancement. A possible mechanism may be the charge-transfer between the metal and the molecules. The enhancement magnitude is estimated to be about $10^2$. This may be site specific and analyte-dependent.

There may be a relationship between electromagnetic enhancement and SERS active substrates. There may need to be certain metal properties. There should be a satisfaction of a localized surface plasma or plasmon resonance (LSPR) condition. For an isolated nanosphere, the wavelength-dependent dielectric constant ($e_m$) of the metal composing the sphere, and the dielectric constant of the local environment around the sphere ($e_0$) may have the relationship "$e_m = -2e_0$". Gold and silver nanoparticles may serve as very good SERS substrates.

The electromagnetic enhancement may also depend on the shape and size of the nanoparticles. Factors such as particle size, shape, and inter-particle spacing may be critical for signal enhancement, and thus high-quality particles would be recommended. Developing a robust detection system may be dependent on the routine production of good quality nanoparticles that can be functionalized with biomolecules. Producing alternatives to spheres, e.g., tri-angles and rods, may have particular relevance and benefit in SERS applications. Many other types of SERS active substrates may be available for varying levels of enhanced surface Raman scattering. Among those, an interesting type of substrate, which appears not to be evident and not yet been reported but may be predicted based on a theoretical description noted herein, may be nanoparticles with intrinsic 3D nanopore structures. This type of SERS active substrates may possess the following advantages. First, the Raman reporter molecules can be immobilized in the nanopores, a very much "hotter" environment (i.e., a place with very high electromagnetic field), thus implying higher electromagnetic enhancement. Secondly, such substrates may possess higher surface area which means more Raman reporter molecules can be immobilized onto a single nanoparticle, potentially increasing the Raman scattering intensity as well.

Chemical enhancement and Raman reporters may also be noted. Raman reporter molecules are immobilized onto the SERS active substrates to produce a strong, characteristic Raman signal that can be easily detected. To ensure the highest enhancement factor, the reporter molecules should reside within the enhanced electromagnetic fields which are generated upon an excitation of the LSPR. Various strategies may be used to confine the analytes to the LSPR enhanced field (less than 2 nm from the substrate surface). These may involve chemisorption, physisorption, partitioning via a self-assembled monolayer, and so on. The self-assembly approach may have advantages for the following reasons. First, the SERS reporters are chemically bonded to the metal surface and therefore are very stable to tolerate a harsh environment in measurement (e.g., high temperature and acidity/base). Secondly, the chemical bonding between the SERS reporters and the metal surface may facilitate the charge transfer process between the two, resulting in favorable chemical enhancement.

Further, the Raman reporter molecules should be capable of producing strong, characteristic Raman signals. A number of different reporters may be available or can be newly designed and synthesized. Typically strong Raman reporters may be organics with distributed electron clouds, such as carbon-carbon double bonds. The pi-electron cloud of the double bond is easily distorted in an external electric field. Bending or stretching the bond changes the distribution of electron density substantially, and causes a large change in induced dipole moment.

Another aspect is associated with addressing the issues of non-specific binding which plague many biomedical diagnostics. A strategy to handle such issues may typically involve the use of a biomolecule resistant coating. For the core-shell nanoparticle SERS optical probes noted herein, the issues may be addressed via incorporating a biomolecule-resisting functionality into the SERS reporters, e.g., a PEG chain. This type of SERS reporters may form a biomolecule-resisting coating around the nanoparticles.

Examples may be noted herein.

Here is an example of the procedures associated with fabrication of the core-shell nanoparticles SERS optical probes. The two newly synthesized compounds, i.e., DSNB and DBPNB, were used as Raman reporters; high aspect ratio gold (Au) nanoparticles were used as SERS active substrates; and desired DNA probes were immobilized onto the nanoparticles. The nanoparticles SERS probes thereof may be useful in ultrasensitive DNA target detections.

Synthesis of SERS reporters may be shown.

5,5'-Dithiobis(succinimidyl-2-nitrobenzoate) (DSNB). To 50 mL of dry tetrahydrofuran were added 0.50 g of dithiobis (2-nitrobenzoic acid) (DNBA) (1.3 mmol), 0.52 g of 1,3-dicyclohexylcarbodiimide (DCCD) (2.5 mmol), and 0.29 g of N-hydroxysuccinimide (NHS) (2.5 mmol) in a 100-mL round-bottom flask equipped with a drying tube. The mixture was magnetically stirred at 25° C. for 12 h, filtered, and then rotary evaporated to remove solvent. The crude product was purified via recrystalization from acetone/hexane, yielding a yellow powder.

5,5'-Dithiobis(Boc-amino PEG amino-2-nitrobenzoamide) (DBPNB). To a solution of DSNB (0.001 mol) in 50 mL dry THF, was added 0.703 g of Boc-amino PEG amine (n=6) (0.0015 mol). The mixture was heated to reflux for 6 hours. Hereafter, the solvent was rotary evaporated, and the crude products thereof were purified via chromatography over silica gel.

5,5'-Dithiobis(amino PEG amino-2-nitrobenzoamide) (DAPNB). To a solution of DBPNB (0.01 mol) in 50 mL dioxane, was added 2 mL of 1 M HCl solution. The mixture was stirred at room temperature for 6 hours. Hereafter the solvent was rotary evaporated, and the crude products were purified via chromatography over silica gel.

Synthesis of gold nanoparticles with 3D nanopore structures may be shown.

An aqueous solution of HAuCl and $AgNO_3$ (5 mL, concentration of $HAuCl_4$ is $1.5 \times 10^{-4}$ M and concentration of $AgNO_3$ is $1.0 \times 10^{-4}$ M) was mixed with a surfactant solution of AOT in hexane (200 mL, AOT concentration is 12 wt-%). Next, 5 mL of 0.1 M $NaBH_4$ was added to the solution under rigorous stirring. The solution color changed immediately upon addition of the reducing agent, indicating particle formation. The reaction was allowed to continue for couple of hours to ensure complete conversion of the metal precursors. The products thereof were purified via dialysis. Specifically, the above products were first dialyzed against a $2.5 \times 10^{-4}$ M tri-sodium citrate solution in acetonitrile followed by further dialysis against a $2.5 \times 10^{-4}$ M tri-sodium citrate solution in deionized water. The tri-sodium citrate is used as the capping agent.

The nanoparticles thereof were then etched in concentrated nitric acid to remove the Ag components, forming the desired Au nanoparticles with intrinsic 3D nanopore structures. Hereafter the crude Au nanoparticles were separated via centrifugation.

Synthesis of High aspect ratio cylindrical gold nanorods may be shown.

Preparation of 3.5 nm seed may be noted. A 20 mL aqueous solution containing $2.5 \times 10^{-4}$ M $HAuCl_4$ and $2.5 \times 10^{-4}$ M tri-sodium citrate was prepared in a conical flask. Next, 0.6 mL of ice cold 0.1 M $NaBH_4$ solution was added to the solution all at once while stirring. The solution turned pink immediately after adding $NaBH_4$, indicating particle formation. The particles in this solution were used as seeds within 2-5 h after preparation. The average particle size measured from the transmission electron micrograph was 3.5 (0.7 nm). Some irregular and aggregated particles were also observed that were not considered for determining the size distribution. Here, citrate serves only as the capping agent since it cannot reduce gold salt at room temperature (25 deg. C.). Experiments performed in the absence of citrate resulted in particles approximately 7-10 nm in diameter.

Preparation of 4.6±1 aspect ratio rod may be noted. In a clean test tube, 10 mL of growth solution, containing 2.5× $10^{-4}$ M $HAuCl_4$ and 0.1 M cetyltrimethylammonium bromide (CTAB), was mixed with 0.05 mL of 0.1 M freshly prepared ascorbic acid solution. Next, 0.025 mL of the 3.5 nm seed solution was added. No further stirring or agitation was done. Within 5-10 min, the solution color changed to reddish brown. The solution contained 4.6 aspect ratio rods, spheres, and some plates. The solution was stable for more than one month.

Procedure for shape separation may be shown. Long rods were concentrated and separated from spheres and surfactant by centrifugation. 10 mL of the particle solution was centrifuged at 2000 rpm for 6 min. The supernatant, containing mostly spheres, was removed and the solid part containing rods and some plates was redispersed in 0.1 mL water.

Preparation of Raman reporter-labeled Au nanoparticles may be shown. The above prepared gold nanoparticles were used. As an example, 100 µL of a mixture of 0.5 mM of DSNB and 2.0 mM of DAPNB solution in acetonitrile was added to 1 mL of the unconjugated colloidal gold suspension and the mixture reacted for hours. The reporter-labeled colloids were then separated from solution by centrifugation. The clear supernatant was discarded, and the loose red sediment was re-suspended in 1 mL of borate buffer (2 mM, pH 9).

DNA immobilization onto the Raman reporter-labeled Au nanoparticles may be shown. Desired DNA probes with an amino group ($-NH_2$) were coupled to the gold particles via the succinimidyl terminus of the DSNB-derived coating. As such, 35 µg of detection DNA probes (7 µL of 5 mg/mL DNA probes solution) was added to the 1-mL suspension of the reporter-labeled colloid. The mixture was then incubated at room temperature for 1 h. Hereafter, it was centrifuged and the supernatant was decanted, the red sediment was resuspended in a desired buffer solution (e.g., 1 mL of 2 mM Tris buffer (Tris-HCl (pH 7.6), 1% BSA)).

Antibody immobilization onto the Raman reporter-labeled Au nanoparticles may be shown. A desired antibody was coupled to the gold particles via the succinimidyl terminus of the DSNB-derived coating. As such, 35 µg of detection antibody (7 µL of 5 mg/mL DAN probes solution) was added to the 1-mL suspension of the reporter-labeled colloid. The mixture was then incubated at room temperature for 1 h. After centrifugation at and removal of the supernatant, the red sediment was re-suspended in 1 mL of 2 mM Tris buffer (Tris-HCl (pH 7.6), 1% BSA).

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A nanoparticle detection system comprising:
    at least one nanoparticle selected from the group consisting of silver, gold and copper, the nanoparticle having 3D intrinsic nanopore structures; and
    a self assembly monolayer shell of organic molecules situated around the nanoparticle, wherein the molecules are SERS reporters; and
    wherein the nanoparticle provides an enhanced surface for Raman scattering (SERS).

2. The system of claim 1, further comprising at least one receptor.

3. The system of claim 2, wherein the receptor ensures selective binding to a target analyte to be measured.

4. The system of claim 1, wherein the shell of molecules may comprise entities for effecting a particular application including attaining certain analyte for SERS analysis.

5. The system of claim 4, wherein the analyte may be organic, chemical, biological, inorganic, gas, liquid or solid.

6. The system of claim 4, wherein a particular application may be effected with:
    DNA probes;
    antibodies;
    oligoglucosides; and/or
    amino acid sequences (RGD receptors).

7. The system of claim 4, wherein a particular application may be effected with chemical, organic, biological, inorganic and/or gas molecules.

8. A nanoparticle SERS probe system comprising:
    a nanoparticle;
    a self assembly monolayer of at least two different types of SERS reporters on the nanoparticle; and
    a biomolecule probe attached to the monolayer.

9. The system of claim 8, wherein:
    the SERS reporters are organic molecules situated around on a surface of the nanoparticle;
    the at least two different types of SERS reporters comprise first and second types of reporters; and
    the first type and second type of reporters are synthesized to have at least one different functional moiety.

10. The system of claim 9, wherein:
    the first type of reporters comprises the following functionalities:
        a binding group to ensure immobilization of the reporters onto the nanoparticle;
        a biomolecule resistant group; and
        a Raman label; and
    the second type of reporters comprises the following functionalities:
        a binding group to ensure immobilization of the reporters onto the nanoparticle;
        a reactive group to react with probes or antibodies; and
        a Raman label.

11. The system of claim 9, wherein the nanoparticle is functionalized for reacting with a desired DNA probe, antibody, oligoglucoside, or amino acid sequence to result in a nanoparticle SERS probe.

12. The system of claim 9, wherein the nanoparticle is functionalized for reacting with a desired organic, chemical, biological, inorganic, gas, and/or like molecule to result in a nanoparticle SERS probe.

13. A nanoparticle SERS probe system comprising:
    a metal nanoparticle;
    a self assembly monolayer containing at least two different types of SERS reporters on the nanoparticle, wherein the SERS reporters are categorized as types according to functionalities;
    a first functionality (a) comprises a binding group to ensure immobilization onto the nanoparticle;
    a second functionality (b) comprises a biomolecule resistant group;
    a third functionality (c) comprises an active group to react with DNA probes, antibodies, oligoglucosides, or an amino acid sequence;
    a fourth functionality (d) comprises a Raman label to produce strong, characteristic Raman signals;

wherein the at least two different types of SERS reporters differ in at least one functionality; and
a biomolecule probe attached to the monolayer.

14. The system of claim 13, wherein a first type of SERS reporters comprises the functionalities (a), (b) and (d), and a second type of SERS reporters comprises functionalities (a), (c) and (d).

15. The system of claim 1, wherein the SERS reporters include at least two of 5,5'-Dithiobis(succinimidyl-2-nitrobenzoate) (DSNB), 5,5'-Dithiobis(Boc-amino PEG amino-2-nitrobenzoamide) (DBPNB), and 5,5'-Dithiobis (amino PEG amino-2-nitrobenzoamide) (DAPNB).

* * * * *